United States Patent [19]
Brisson

[11] 4,248,217
[45] Feb. 3, 1981

[54] INHALATION HEATER CONTROL

[75] Inventor: A. Glen Brisson, Arlington Heights, Ill.

[73] Assignee: Respiratory Care, Inc., Arlington Heights, Ill.

[21] Appl. No.: 89,320

[22] Filed: Oct. 30, 1979

[51] Int. Cl.³ .......................................... A61M 16/00
[52] U.S. Cl. ......................... 128/204.17; 128/203.27
[58] Field of Search ..................... 128/204.17, 203.17, 128/203.14, 203.26, 203.27, 204.21, 207.15

[56] References Cited
U.S. PATENT DOCUMENTS

| 3,871,371 | 3/1975 | Weigl | 128/204.17 |
| 4,034,740 | 7/1977 | Atherton et al. | 128/1 B |

Primary Examiner—Henry J. Recla
Attorney, Agent, or Firm—Eric P. Schellin

[57] ABSTRACT

For use in inhalation therapy, a system for raising inhalation temperature which senses both inhalation and exhalation temperatures. In one mode of operation, the inhalation temperature is continuously raised, while the time sequence of inhalation and exhalation temperatures is recorded. In another mode of operation, the inhalation temperature is made to track, at a constant lower offset, the exhalation temperature.

7 Claims, 7 Drawing Figures

INHALATION HEATER CONTROL

BACKGROUND OF THE INVENTION

This invention relates in general to gas inhalation therapy and more particularly to the controlled heating of gas inspired by a patient through a respirator.

Conventionally, the gas delivered to a patient during surgery, for example, is heated by a heater under control of a temperature sensor probe at some location in the inhalation path. Thus, inhaled air may be warmed to a predetermined temperature in order to supply a regulated quantity of heat to the patient. By means of a read-out device connected to the sensor probe, the temperature of the inhaled air may be monitored. However, because of variations in the body core temperature, an excess amount of heat is sometimes absorbed by the patient causing heat stress.

It is therefore an important object of the present invention to provide an improved temperature controlled heater for inhaled gas delivered by a respirator wherein the supply of excess heat is automatically prevented.

SUMMARY OF THE INVENTION

In accordance with the present invention, temperature sensing gas probes such as thermistors are placed in both the inhalation and exhalation flow paths of a respirator to monitor variations in inhalation and exhalation temperatures caused by changes in body core temperature as well as to automatically control the output of the inhalation heater so that the inhalation temperature will track below the exhalation temperature with a substantially constant offset or separation that is adjustable. The heater is electrically energized by an AC power source through a power isolating drive component such as an optionally coupled triac to which a signal input is fed from a modulator receiving the output of a comparator such as a differential amplifier. Electronic thermometers connected to the gas sensing probes supply temperature input signals to the two input terminals of the comparator in order to produce an output therefrom producing the exhalation temperature tracking control over the heater as aforementioned. By means of a trip circuit connected to the inhalation temperature input of the comparator, the output of the heater may be limited to an upper limiting temperature for the inhaled air, such as 40° C. By means of a mode selection switch assembly, operation of the heater may be manually switched from its automatic tracking mode to either a set mode wherein the inhaled air temperature is preset or a diagnostic mode wherein the inhaled temperature is increased from a lower limit to a peak value during a test run.

To prevent premature automatic tracking operation before the patient is intubated, an inhibit circuit is provided to prevent tracking until the exhalation temperature is above a lower limit, such as 28° C.

THE DRAWINGS

Figure 6:
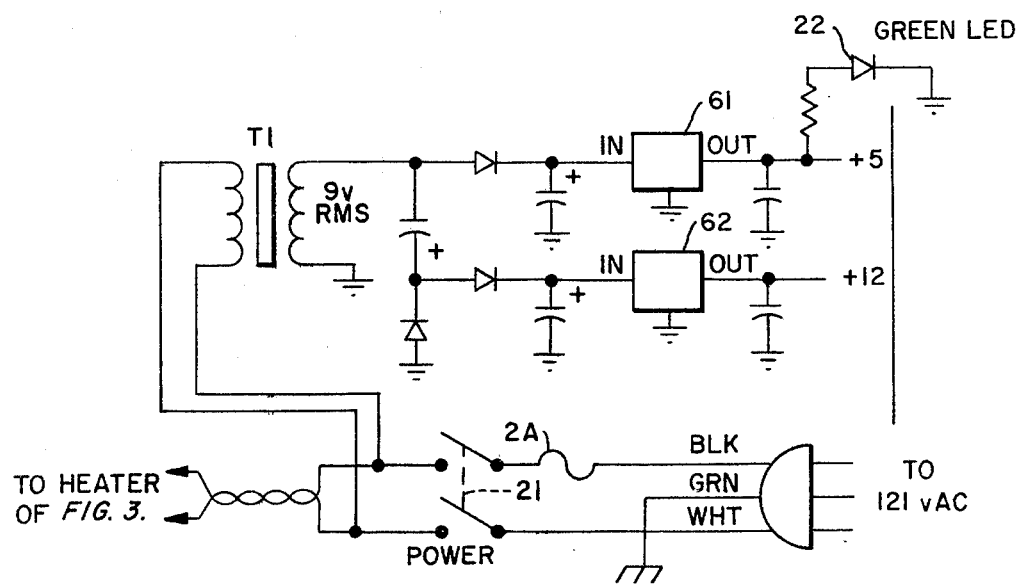
FIGS. 3 to 6 are circuit diagrams of the four portions of the equipment associated with the control panel of FIG. 2, as follows.
Figure 3:
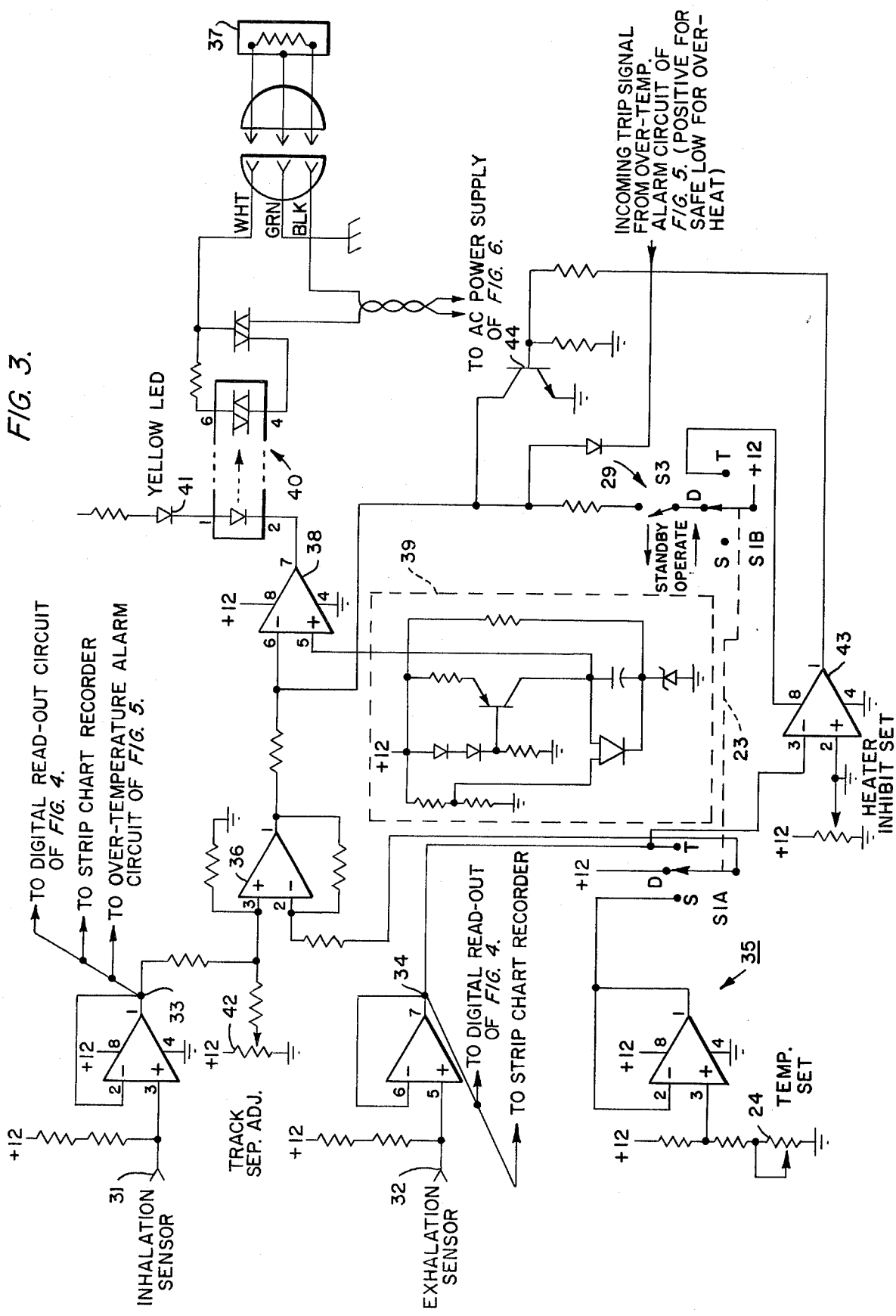
Figure 4:
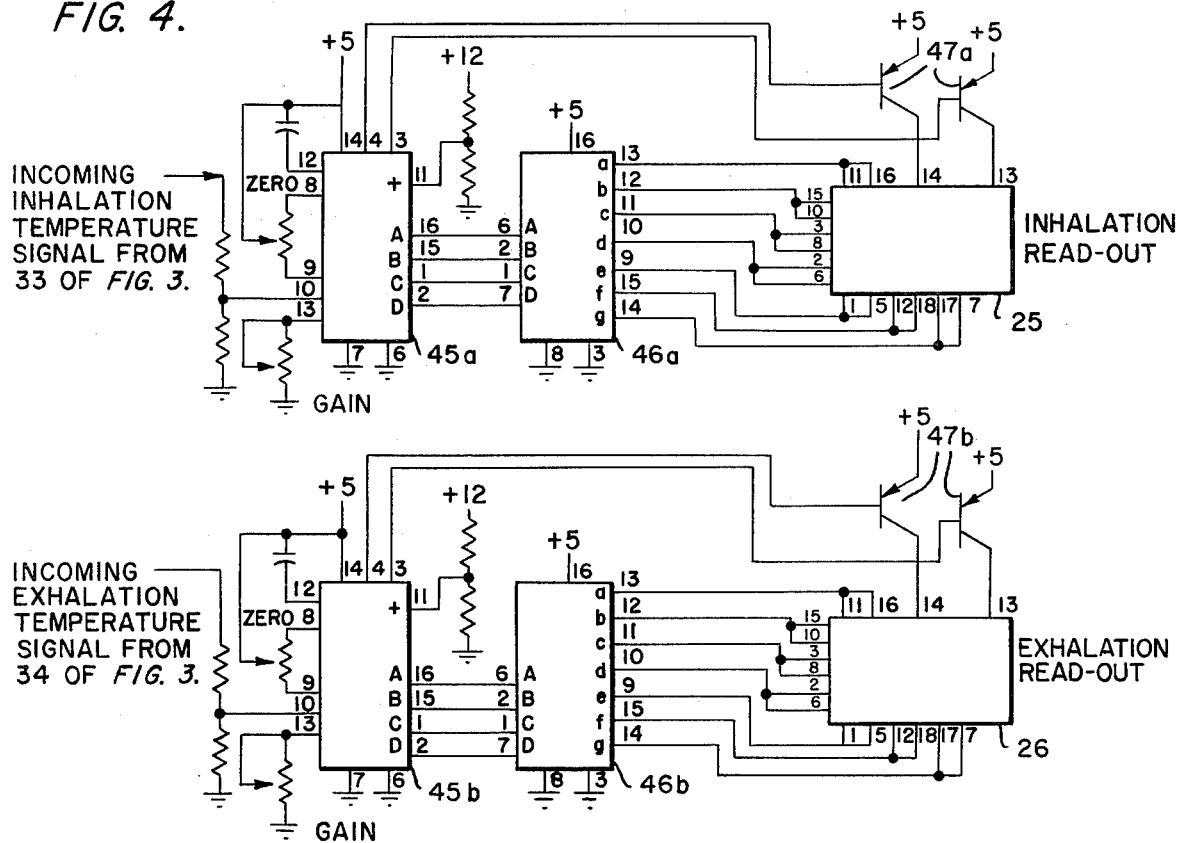
Figure 5:
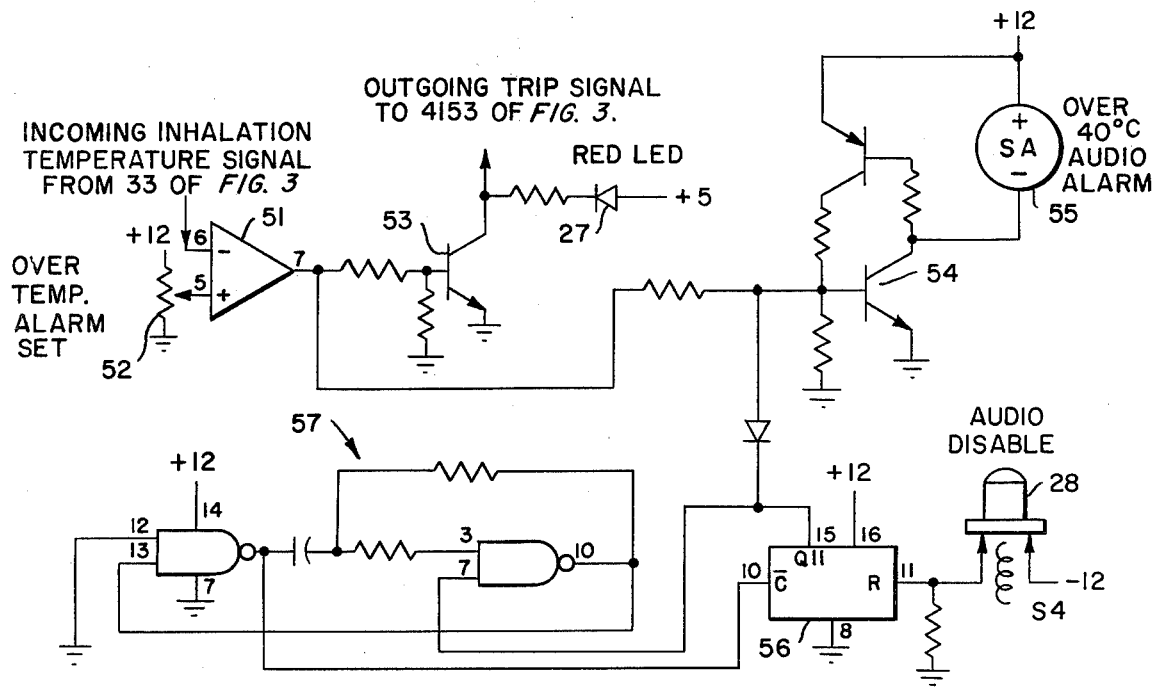

FIG. 3 relates to temperature control.
FIG. 4 relates to temperature read-out.
FIG. 5 relates to overtemperature alarm and automatic heater shut-down.
FIG. 6 relates to power supply.

Figure 7:
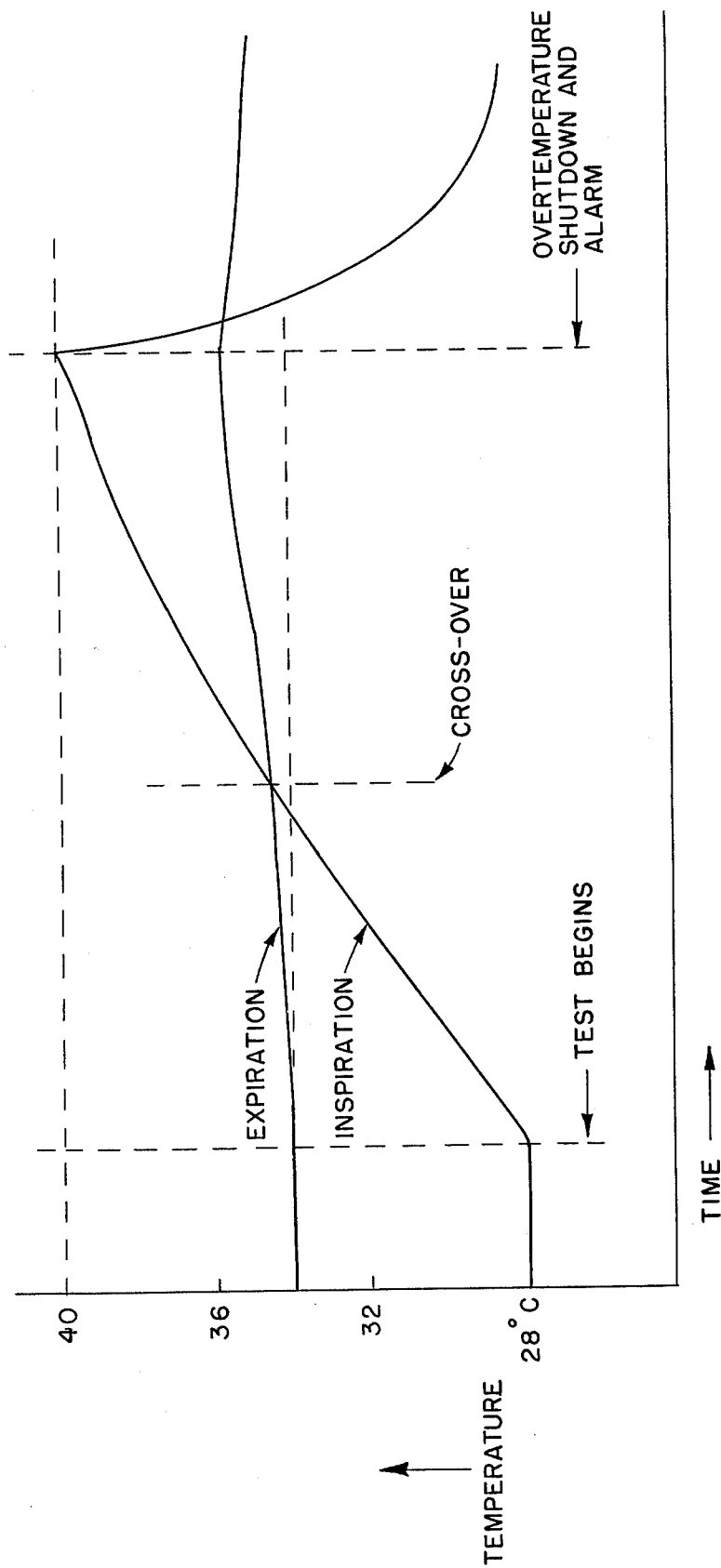

FIG. 7 is a graph showing the results of a typical diagnostic test.

In accordance with the inventive concept, during inhalation therapy or diagnosis, the temperature of both inhalation and exhalation are important and must be sensed. In order to sense the temperature of inhalation independently of the sensing of the temperature of exhalation, the inhalation and exhalation flows are channeled into separate paths.

Figure 1:
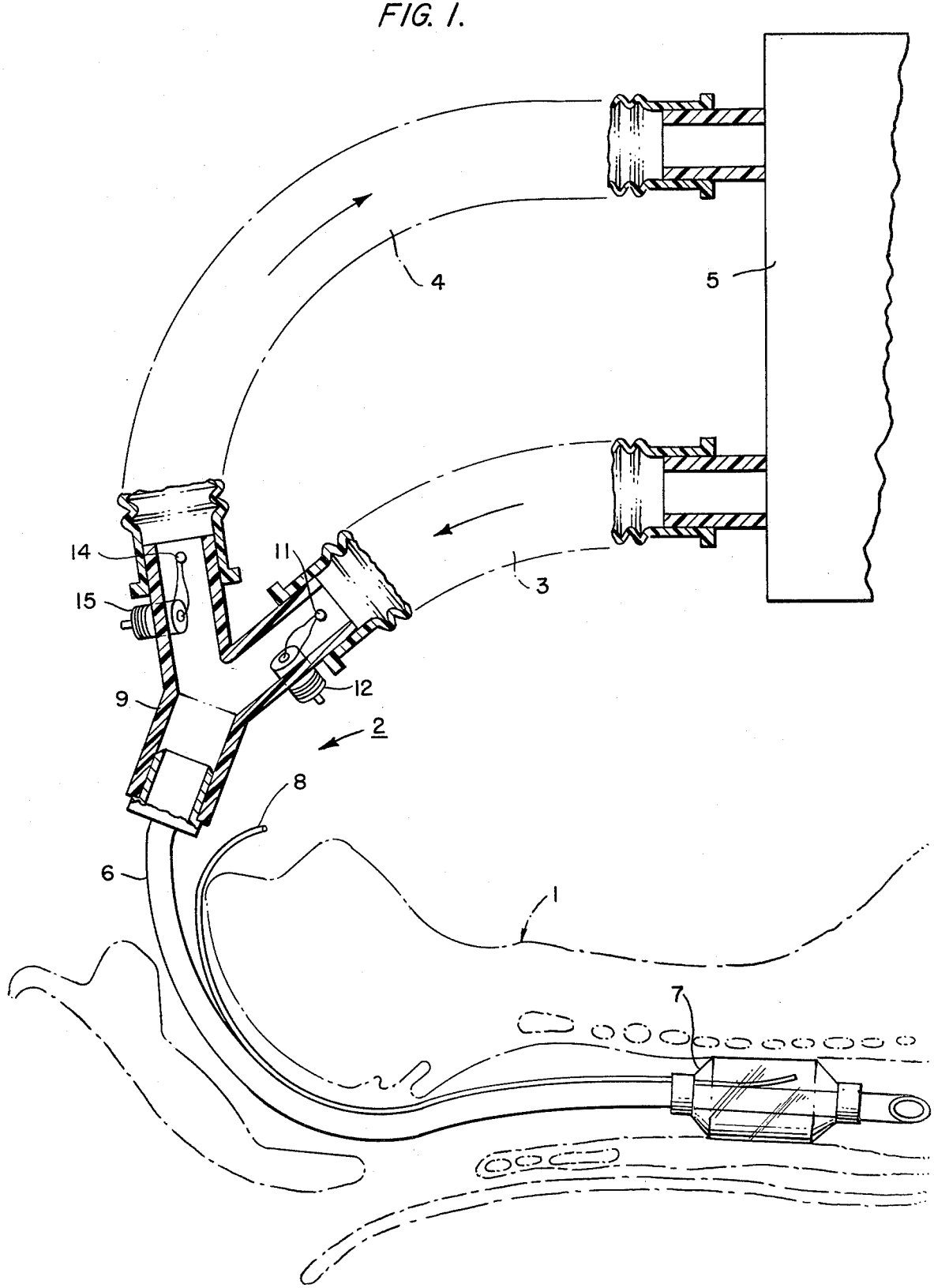
FIG. 1 shows a patient connected, by way of an intubation tube and inhalation and exhalation hoses, to a volume ventilator and inhalation therapy apparatus.

In FIG. 1 the invention is illustrated for the particular case where the patient is connected to the inhalation apparatus by way of intubation. The patient 1 is shown lying supine with chin extended to straighten the patient's airway. The intubation means 2 includes an endotracheal tube 6 which is lodged at the proper place in the trachea by means of a cuff 7. The cuff 7 is inflated in a well known manner through tube 8. The inflation apparatus and ancillary devices, such as a pilot balloon, are not shown. The endothracheal tube 6 terminates, close to the mouth, in a wye 9, having two branches. One branch leads to inhalation airway 3 while the other branch leads to exhalation airway 4. In order to channel the oscillating flow in intubation tube 6 into two one-way flows, check valve means, not shown, are provided for each of airways 3 and 4. The check valves must be light in order to respond properly to low breathing pressures. The check valves may be included in the wye 9, or they may be included in the volume ventilator and inhalation therapy apparatus 5, where the gravity effect on their operation would not change with the attitude of the wye 9.

The details of the airways and check valves are similar to those in rebreathing apparatus used by firefighters and astronauts, and are similar to those used in metabolism testing machines, and need not be further described.

Although the invention has been illustrated in connection with intubation it is to be understood that a face mask or analagous non-invasive means may be used.

In the volume ventilator and inhalation therapy apparatus 5 there are various means to feed air, oxygen, water mist or vapor, or medication to the inhalation airway 3; and there is an electric heater to warm what is fed. This is well known in the prior art, and need not be further described.

In accordance with the invention, temperature sensing means are provided in each of the exhalation and inhalation paths to control the electric circuit for the electric heater. These temperature sensing means are thermistors 11 and 14, connected to coaxial connectors 12 and 15. It will be evident, from the location of thermistors 12 and 14, and from the direction of flow in airways 3 and 4, that thermistor 12 responds to inhalation temperature while thermistor 14 responds to exhalation temperature.

Figure 2:
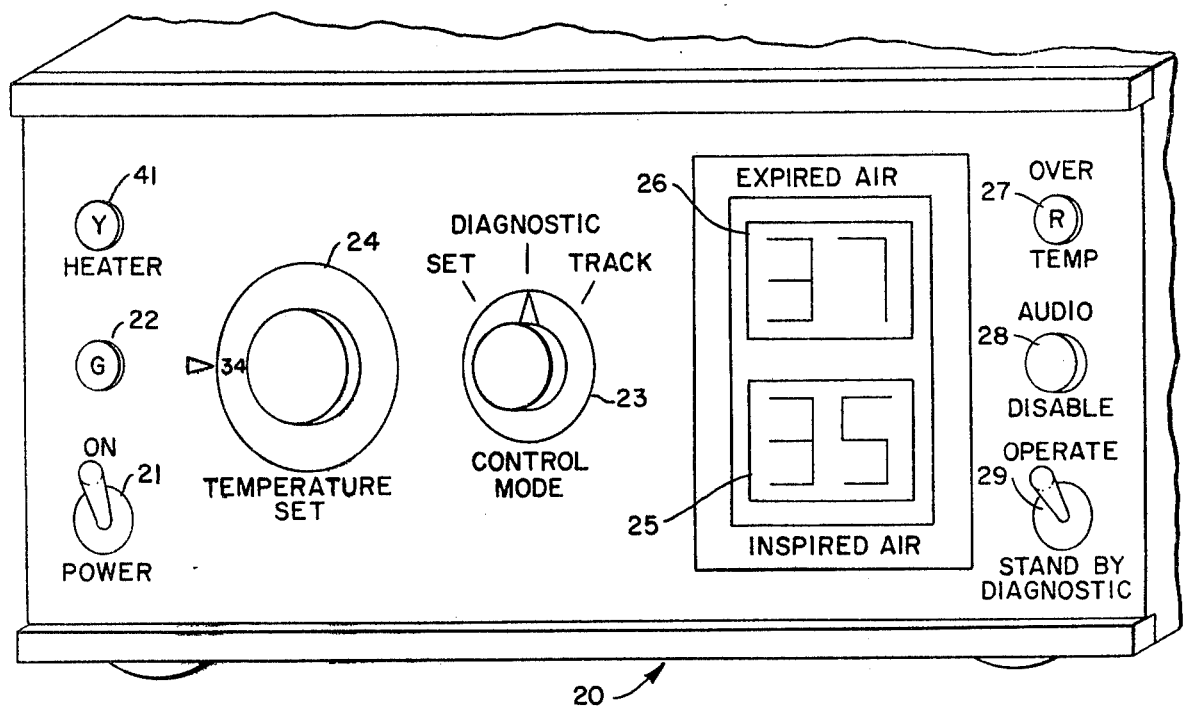
FIG. 2 is a view of the control panel which is connected with the temperature aspects of the inhalation therapy.

FIG. 2 illustrates the control and indicator panel 20 associated with apparatus 5. The panel 20 has an on-off power switch 21 which controls energization of the circuits. When "on", the green indicator 22 glows. A mode switch 23 controls which one of three different operating modes is selected. When the "set" mode is selected, the temperature set potentiometer 24 determines the regulated temperature of inhalation. The actual temperatures of inhalation and expiration are indicated by the displays 25 and 26, respectively.

An over-temperature indicator 27 glows whenever the inhalation temperature exceeds a given level, chosen, in the illustrated embodiment, to be 40° C. When the over-temperature indicator 27 glows, an audible alarm, not shown, sounds. It can be disabled for a measured time period by depressing the push button 28.

The "diagnostic" and "track" settings of mode switch 23 and of the operate-standby switch 29 will be explained below, when the details of the pertinent circuits are discussed.

FIG. 3 shows the temperature control portion of the electric circuit, used to control an electric heater 37, located in the inhalation pneumatic circuit from volume ventilator 5 to endotracheal tube 6. The thermistors 11 and 14 of FIG. 1 are connected through coaxial connectors 12 and 15, respectively, to input connectors 31 and 32, respectively, of FIG. 3.

It is to be understood that themocouples with controlled reference junctions may be substituted for the thermistors. The input connectors 31 and 32 control respective voltage following operational amplifiers which provide, at outputs 33 and 34, stable voltages which are, respectively, measures of inhalation and exhalation temperatures.

Let it be assumed that mode switch 23 is in the "set" position. Then voltage source 35 delivers to the inverting input of differential amplifier 36 a fixed voltage determined by the temperature set potentiometer 24. Meanwhile output 33 delivers to the noninverting input of differential amplifier 36 a voltage proportional to the inhalation temperature. The output of differential amplifier 36 is thus a voltage roughly linearly proportional to the departure of inhalation temperature from that set by the potentiometer 24, between the limits when differential amplifier 36 saturates or bottoms.

The linear output of differential amplifier 36 is of low power and cannot directly control or energize electric heater 37, which is of considerable power and is supplied from the 121 volt source of FIG. 6. Accordingly, the said linear output is converted by modulator 38 to width modulated high-low pulses. This is accomplished by feeding to the lower input of modulator 38 a saw tooth voltage obtained from saw tooth oscillator 39.

The pulse width modulated high-low pulse train from modulator 38 drives the optically coupled triac 40 which drives the Q4004, which energizes the electric heater 37 in pulse width manner. Everytime the electric heater 37 is energized, yellow diode 41 glows. Thus, in the "set" mode, the temperature of the electric heater is maintained continuously at the temperature predetermined by the physician and controlled by the adjustment of set potentiometer 24.

It is to be noted that the use of pulse width modulation to control the heating of electric heater 37 ensures that the control will be essentially proportional over a considerable range, and will also prevent problems of thermal hunting, caused by thermal resistance and thermal inertia in non-proportional control systems.

When mode switch 23 is set to the "diagnostic" position, the positive 12 volts applied by way of switch wafer S1A to the inverting input of differential amplifier 36 effectively disconnects the output of differential amplifier 36 from the input of modulator 38. At the same time, if standby-operate switch 29 is in the "operate" position, positive 12 volts is applied to the input of modulator 38 by way of switch wafer S1B to produce a maximum constant heating of the electric heater 27. In this mode the resulting temperatures as recorded by strip-chart recorders attached to the outputs 33 and 34 would have an appearance, for one patient, which is shown in FIG. 7. It will be noted that, after the test begins, the inhalation temperature goes up monotonically from an ambient temperature of 28° C. until the test is ended, when the inhalation temperature has risen to 40° C. At the point of cross-over, indicated in FIG. 7, the heat balance of the patient, for breathing alone, is zero. This point is considered to be of considerable medical significance.

The operate-standby switch 29 is useful since it permits the strip-charts and other equipment to be set up at leisure and then permits initiation of the test, as illustrated in FIG. 7, by more flipping up of the switch 29.

When mode switch 23 is set into the "track" position the outputs 33 and 34 are connected to the two inputs of differential amplifier 36. In this mode the inhalation temperature is made to track at a temperature lower than the exhalation temperature. The amount of the offset is determined by the input from potentiometer 42. In order that the equipment does not become active in the track mode before the patient has been intubated, an inhibit circuit is provided for inactivating the circuit whenever the exhalation temperature is below 28° C., indicating that intubation has not occurred. The inhibit circuit includes differential amplifier 43, which provides a positive output to the base of transistor 44, to thereby bottom the inverting input and raise the output of modulator 38, which, in turn, shuts off the optically coupled triac 40 and the heater 37.

The outputs 33 and 34 are used to activate the inhalation and exhalation temperature readouts 25 and 26, respectively, of FIG. 2. This is done with the circuitry of FIG. 4.

The signal from output 33 is applied to the input of analog-to-digital converter 45a, which controls a decoder 46a and transistor drivers 47a. The decoder 46a and transistor drivers 47a control two decades of seven segment decimal displays in the inhalation read-out 25. The operation of these displays is well understood in the art and will not be further elaborated. The signal from output 34 is similarly applied to the input of analog-to-digital converter 45b to control the exhalation read out 26 by way of decoder 46b and transistor drivers 47b.

A patient would be in danger if the inhalation temperature went too high. Accordingly, the circuitry of FIG. 5 is provided to automatically shut down the electric heater system if the inhalation temperature exceeds a predetermined amount, such as 40° C. An audio alarm also sounds when this occurs.

The output 33 is connected to the inverting input of operational amplifier 51, whose noninverting input is supplied from over-temperature alarm set potentiometer 52 with a reference voltage which determines the alarm trigger limit. When inhalation temperature is too high, the output of differential amplifier 51 goes high, thereby turning on transistors 53 and 54 to respectively light up the overtemperature indicator 27 and audio alarm 55.

Furthermore, the voltage on the collector of transistor 53, which is low under alarm conditions, is fed through the IN4153 diode of FIG. 3 to the inverting input of modulator 38. This turns off the electric heater 37, so that inhalation temperature cannot rise further.

An audio disable button 28 is provided to silence the audio alarm 55 for a fixed period. When depressed, the button 28 resets the ripple counter 56 so that its output at pin 15 goes low. The low voltage is connected by an obvious path to transistor 54 to turn it, and therefore the audio alarm 55, off. However, this low voltage is ineffective to turn off the alarm indicator 27 because of the presence of the 82 kilo ohm resistor.

The ripple counter, when reset to turn the alarm off, also energizes multivibrator 57 at the lower pin of 1C12B. The multivibrator pulses are fed to pin 10 of the ripple counter 56, which counts up to its designed count, and then sets itself to deliver a high output at pin 15. The high output again makes the audio alarm 55 operative and shuts off the multivibrator 57.

The power supply of FIG. 6 includes two voltage regulators to provide constant 5 and 12 volt positive biases. The "on" visual indicator 22 alerts as to the setting of on-off switch 21.

I claim:
1. An inhalation heater control comprising:
   means providing separate closed respiratory airway paths to and from a patient;
   electric heater means to provide heat in the inhalation airway path;
   means in each of the airway paths to respectively sense inhalation temperature and exhalation temperature; and
   means responsive to said sensing means to cause the electric heater means to emit heat in the inhalation path in such degree that the inhalation temperature tracks the exhalation temperature within a predetermined temperature difference.
2. The inhalation heater control of claim 1 comprising:
   means to cause the electric heater means to monotonically raise the inhalation temperature and
   means to separately record the sensed inhalation and exhalation temperatures.
3. The inhalation heater control of claim 2 comprising:
   means to automatically cause the electric heater means to discontinue heating when the inhalation temperature has reached a predetermined level.
4. The inhalation heater control of claim 1 comprising:
   means to cause the tracking to be such that the inhalation temperature is offset and lower than the exhalation temperature by a fixed temperature difference.
5. The method of controlling the temperature of inhalation of a patient so that it is at a level just below that which would subject the patient to heat stress, which method consists of the steps of:
   measuring the temperature of inhalation;
   measuring the temperature of exhalation; and
   controlling the temperature of inhalation so that it tracks the temperature of exhalation with a constant temperature offset, with the former temperature lower than the latter.
6. The method of claim 5 in which said constant temperature offset is approximately 2° Centigrade.
7. In a control system for an inhalation heater having means for monitoring the temperature of gas inhaled, means for regulating the amount of heat delivered by the heater including sensor means for simultaneously measuring the temperature of the gas inhaled and exhaled, and means connected to said sensor means for controlling operation of the heater producing an inhalation temperature tracking the exhalation temperature of the gas exhaled within a predetermined temperature difference.

* * * * *